US012742783B2

(12) United States Patent
Hata et al.

(10) Patent No.: US 12,742,783 B2
(45) Date of Patent: Sep. 22, 2026

(54) METHOD OF EVALUATING FUNCTION OF ORGAN FOR TRANSPLANTATION, PROGRAM FOR EVALUATING FUNCTION OF ORGAN FOR TRANSPLANTATION, AND APPARATUS THAT EVALUATES FUNCTION OF ORGAN FOR TRANSPLANTATION

(71) Applicants: Shimadzu Corporation, Kyoto (JP); KYOTO UNIVERSITY, Kyoto (JP)

(72) Inventors: Koichiro Hata, Kyoto (JP); Hidetaka Miyauchi, Kyoto (JP); Hideshi Fujiwake, Kyoto (JP); Minoru Kashihara, Kyoto (JP); Takeru Kunimitsu, Kyoto (JP)

(73) Assignees: SHIMADZU CORPORATION, Kyoto (JP); KYOTO UNIVERSITY, Kyoto (JP)

(*) Notice: Subject to any disclaimer, the term of this patent is extended or adjusted under 35 U.S.C. 154(b) by 209 days.

(21) Appl. No.: 17/624,956

(22) PCT Filed: Jul. 1, 2020

(86) PCT No.: PCT/JP2020/025761

§ 371 (c)(1),
(2) Date: Jan. 5, 2022

(87) PCT Pub. No.: WO2021/006135

PCT Pub. Date: Jan. 14, 2021

(65) Prior Publication Data

US 2022/0291225 A1 Sep. 15, 2022

(30) Foreign Application Priority Data

Jul. 8, 2019 (JP) ................................ 2019-126886

(51) Int. Cl.
*G01N 33/68* (2006.01)
*G01N 33/66* (2006.01)

(52) U.S. Cl.
CPC ............. *G01N 33/68* (2013.01); *G01N 33/66* (2013.01)

(58) Field of Classification Search
CPC .... G01N 33/68; G01N 33/66; G01N 33/6893; G01N 2800/08; G01N 2800/245; G01N 33/6848; G01N 27/62; G01N 33/82; A01N 1/02; A01N 1/10; C12M 1/34; C12Q 1/02
See application file for complete search history.

(56) References Cited

U.S. PATENT DOCUMENTS

2009/0155826 A1* 6/2009 Hu ...................... G01N 33/487 435/14
2012/0315618 A1 12/2012 Kravitz et al.
2013/0210665 A1 8/2013 Sanchez Fueyo et al.
2015/0289499 A1 10/2015 Tsuji et al.
2017/0370954 A1* 12/2017 Perichon ........... G01N 33/5023

FOREIGN PATENT DOCUMENTS

CN 103154267 6/2013
JP 2018-154617 10/2018
WO 2015/042602 3/2015

OTHER PUBLICATIONS

Memorandum: "Recent Subject Matter Eligibility Decision: *Vanda Pharmaceuticals Inc.* v. *West-Ward Pharmaceuticals*" form Robert Bahr, dated Jun. 7, 2018. (Year: 2018).*
Office Action issued Dec. 20, 2022 in Japanese Patent Application No. 2021-530638, with English-language translation.
Extended European Search Report issued May 24, 2023 in corresponding European Patent Application No. 20836132.9.
Cornelia J. Verhoeven et al., "Biomarkers to assess graft quality during conventional and machine preservation in liver transplantation", Journal of Hepatology, vol. 61, pp. 672-684, 2014.
Karim Hamaoui et al., "Rapid sampling microdialysis as a novel tool for parenchyma assessment during static cold storage and hypothermic machine perfusion in a translational ex vivo porcine kidney model", Journal of Surgical Research, vol. 200, pp. 332-345, 2016.
C.R. Parikh et al., "Association of Perfusate Biomarkers and Pump Parameters with Delayed Graft Function and Deceased Donor Kidney Allograft Function", American Journal of Transplantation, vol. 16, pp. 1526-1539, 2016.
Aono et al., "A pentose bisphosphate pathway for nucleoside degradation in Archaca", Nature Chemical Biology, 2015, 11(5). pp. 355-360.
Yoshida et al., "Gastroenterological Cancer Diagnosis by Metabolomics-Discovery of Pancreatic Cancer Biomarker" Rinsho Byori, The Official Journal of Japanese Society of Laboratory Medicine, 2015, 63 (4), pp. 450-456, with machine translation.
Office Action issued Jun. 27, 2023 in corresponding Japanese Patent Application No. 2021-530638, with English-language translation.
Office Action issued Mar. 5, 2024 in European Patent Application No. 20 836 132.9.

(Continued)

*Primary Examiner* — Lyle Alexander
*Assistant Examiner* — Alison Claire Gerhard
(74) *Attorney, Agent, or Firm* — Wenderoth, Lind & Ponack, L.L.P.

(57) ABSTRACT

A method of evaluating a function of an organ for transplantation harvested from a living body, the method includes preparing data representing change over time in content of marker substances in accordance with a perfusion, taking a first tissue sample from the organ for transplantation at first timing in a reperfusion of the organ for transplantation, taking a second tissue sample from the organ for transplantation at second timing after the first timing in the reperfusion, measuring contents of the marker substances in the first tissue sample, measuring contents of the marker substances in the second tissue sample, calculating change in content at the second timing as compared with the first timing for each of the marker substances, and calculating an indicator relating to evaluation of the function of the organ for transplantation using the calculated change in content and the data.

8 Claims, 11 Drawing Sheets

(56) References Cited

OTHER PUBLICATIONS

Office Action issued Mar. 21, 2024 in Chinese Patent Application No. 202080049427.4, with English-language Translation.

Japanese Office Action issued Dec. 22, 2023 in corresponding Japan Patent Application No. 2021-530638, with English machine translation.

Office Action issued Dec. 24, 2024 in Japanese Patent Application No. 2023-16110, with English-language Translation.

Notice of Reasons for Refusal drafted Jul. 29, 2024 and mailed on Jul. 30, 2024 in Japanese Patent Application No. 2021-530638.

Office Action issued Feb. 26, 2025 in corresponding Chinese Patent Application No. 202080049427.4, with English-language translation.

* cited by examiner

FIG.2

FIG.4
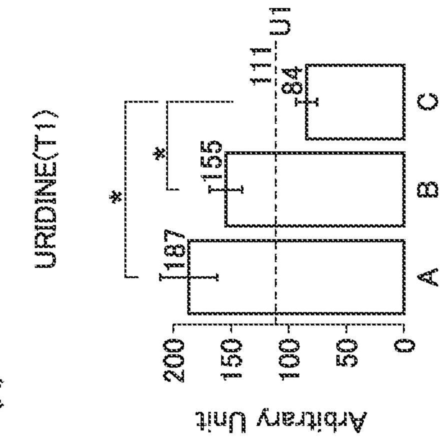
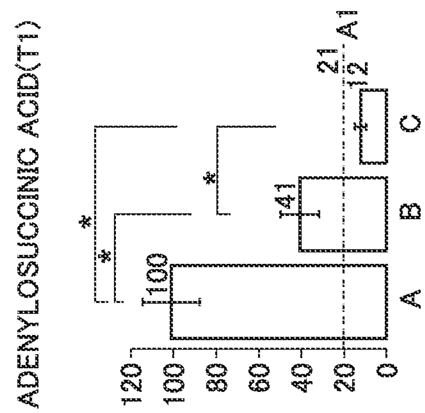
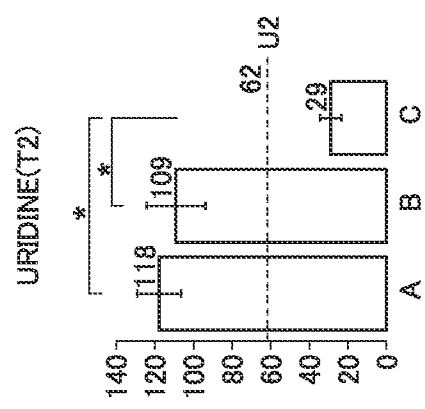

(A) SEDOHEPTULOSE 7-PHOSPHATE
(B) ADENOSINE TRIPHOSPHATE
(C) GLUCOSE-6-PHOSPHATE
(D) SUCCINYL CoA
(E) DIMETHYLGLYCINE
(F) CHOLINE
(G) 2-AMINOBUTYRIC ACID
(H) URIC ACID
(I) PYRUVIC ACID
(J) INOSINE
Arbitrary Unit
Arbitrary Unit
A(T3) A(T4) B(T3) B(T4) C(T3) C(T4)

FIG.6

| METABOLITE | A1 | A2 | A3 | A4 | A5 | B1 | B2 | B3 | B4 | B5 | C1 | C2 | C3 | C4 | C5 |
|---|---|---|---|---|---|---|---|---|---|---|---|---|---|---|---|
| SEDOHEPTULOSE 7-PHOSPHATE | 1 | 0 | 1 | 0 | 0 | 1 | 1 | 1 | 1 | 1 | 0 | 0 | 0 | 0 | 0 |
| ADENOSINE TRIPHOSPHATE | 0 | 0 | 0 | 0 | 0 | 1 | 1 | 1 | 1 | 1 | 0 | 0 | 0 | 0 | 0 |
| GLUCOSE-6-PHOSPHATE | 1 | 1 | 1 | 1 | 1 | 1 | 1 | 1 | 1 | 1 | 0 | 0 | 0 | 0 | 1 |
| SUCCINYL CoA | 1 | 0 | 1 | 1 | 1 | 1 | 1 | 1 | 1 | 1 | 1 | 1 | 1 | 0 | 0 |
| DIMETHYLGLYCINE | 1 | 1 | 1 | 1 | 1 | 1 | 1 | 1 | 1 | 1 | 0 | 0 | 0 | 0 | 0 |
| CHOLINE | 1 | 1 | 1 | 1 | 1 | 1 | 1 | 1 | 1 | 1 | 0 | 0 | 0 | 0 | 0 |
| 2-AMINOBUTYRIC ACID | 1 | 1 | 1 | 1 | 1 | 1 | 1 | 1 | 1 | 1 | 0 | 0 | 0 | 0 | 0 |
| URIC ACID | 1 | 1 | 1 | 1 | 1 | 1 | 1 | 1 | 1 | 1 | 0 | 0 | 0 | 0 | 0 |
| PYRUVIC ACID | 1 | 1 | 1 | 0 | 1 | 1 | 1 | 0 | 1 | 1 | 0 | 0 | 0 | 0 | 0 |
| INOSINE | 0 | 1 | 1 | 0 | 1 | 1 | 1 | 1 | 1 | 1 | 0 | 0 | 0 | 0 | 0 |
| TOTAL SCORE | 8 | 7 | 9 | 6 | 8 | 10 | 10 | 9 | 10 | 10 | 1 | 1 | 1 | 0 | 1 |

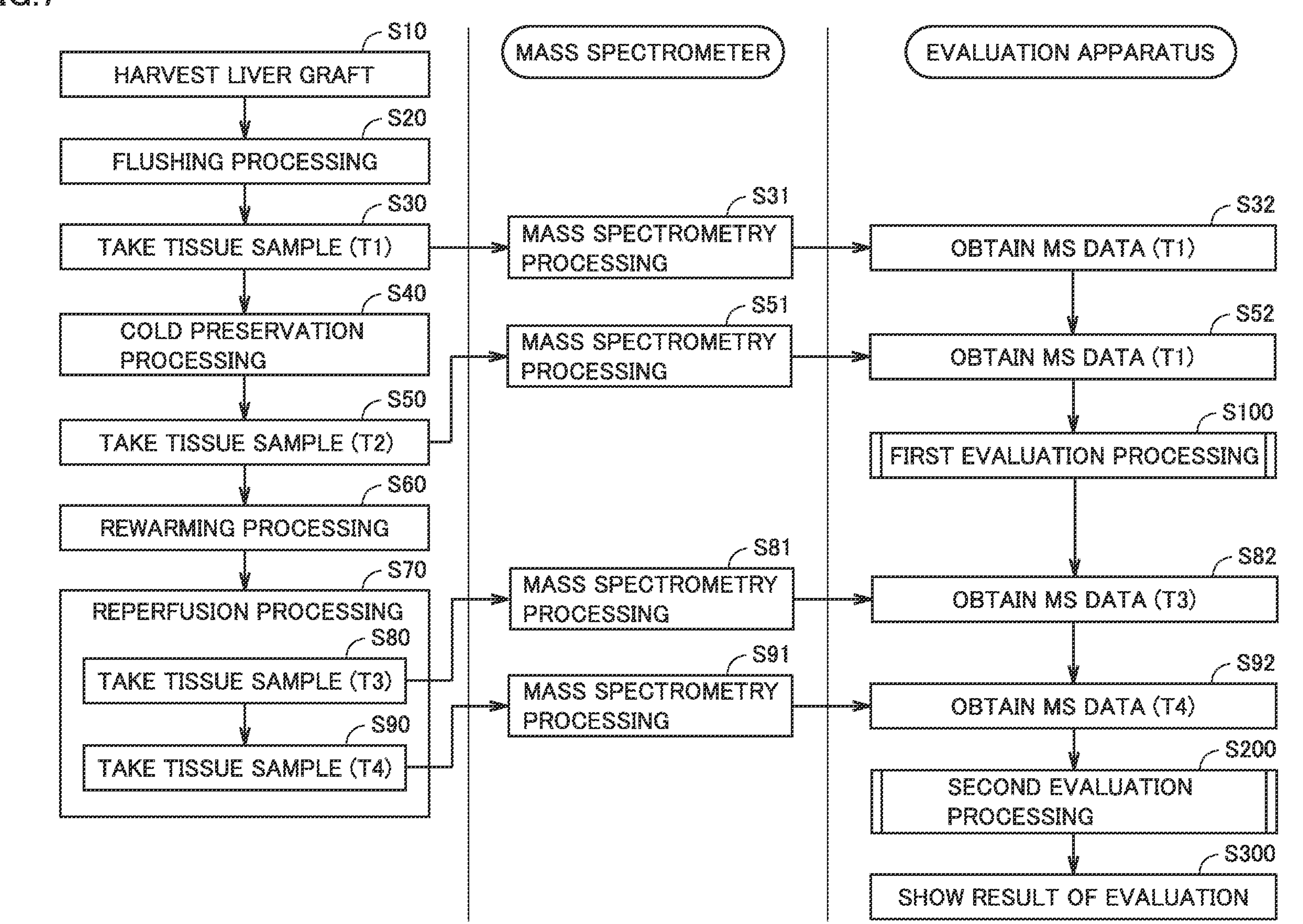
FIG.7
MASS SPECTROMETER
EVALUATION APPARATUS
S10 HARVEST LIVER GRAFT
S20 FLUSHING PROCESSING
S30 TAKE TISSUE SAMPLE (T1)
S40 COLD PRESERVATION PROCESSING
S50 TAKE TISSUE SAMPLE (T2)
S60 REWARMING PROCESSING
S70 REPERFUSION PROCESSING
S80 TAKE TISSUE SAMPLE (T3)
S90 TAKE TISSUE SAMPLE (T4)
S31 MASS SPECTROMETRY PROCESSING
S51 MASS SPECTROMETRY PROCESSING
S81 MASS SPECTROMETRY PROCESSING
S91 MASS SPECTROMETRY PROCESSING
S32 OBTAIN MS DATA (T1)
S52 OBTAIN MS DATA (T1)
S100 FIRST EVALUATION PROCESSING
S82 OBTAIN MS DATA (T3)
S92 OBTAIN MS DATA (T4)
S200 SECOND EVALUATION PROCESSING
S300 SHOW RESULT OF EVALUATION

METHOD OF EVALUATING FUNCTION OF ORGAN FOR TRANSPLANTATION, PROGRAM FOR EVALUATING FUNCTION OF ORGAN FOR TRANSPLANTATION, AND APPARATUS THAT EVALUATES FUNCTION OF ORGAN FOR TRANSPLANTATION

TECHNICAL FIELD

The present invention relates to a method of evaluating a function of an organ for transplantation, a program for evaluating a function of an organ for transplantation, and an apparatus that evaluates a function of an organ for transplantation.

BACKGROUND ART

Japanese Patent Laying-Open No. 2018-154617 (PTL 1) discloses as a technology for overcoming chronic organ shortages in transplantation medical care, a method for long-term preservation while maintaining the function of an organ for transplantation. PTL 1 enables recovery of an organ from a cardiac arrest donor to a state close to a state before cardiac arrest by perfusion with a perfusate containing an oxygen carrier and a blood coagulation inhibitor for suppressing tissue disorder accompanying warm ischemia.

CITATION LIST

Patent Literature

PTL 1: Japanese Patent Laying-Open No. 2018-154617

SUMMARY OF INVENTION

Technical Problem

In conventional organ transplantation, determination as to whether or not an organ for transplantation is transplantable is exclusively based on experiences (tacit knowledge) of a transplantation surgeon and prompt histopathological diagnosis. If an organ that is determined as being transplantable based on tacit knowledge of a transplantation surgeon but does not actually function is transplanted, primary non-function (PNF) may be caused. In particular, after transplantation of heart, lung, and liver that are called vital organs, a patient may die unless retransplantation is quickly carried out.

Thus, in a conventional method, there is no objective criterion for determining a potential function of an organ or a degree of irreversible damage to an organ. Therefore, suitability of an organ cannot accurately be determined prior to transplantation and determination has been entrusted to an experienced transplantation surgeon. Therefore, an organ harvested from a cardiac arrest donor, a function of which has been recovered by the technology described in PTL 1, may ultimately be determined as not being transplantable in consideration of PNF, and there is a concern that a check may be imposed on solution of lack of donors. Even when transplantation is carried out, graft loss may occur due to PNF and there is always possibility of losing a patient.

This invention was made to solve such problems, and an object thereof is to provide an indicator for objectively evaluating transplantability of an organ for transplantation.

Solution to Problem

A method of evaluating a function of an organ for transplantation harvested from a living body according to a first aspect of the present invention includes preparing data representing change over time in contents of marker substances in accordance with a perfusion, taking a first tissue sample from the organ for transplantation at first timing in a reperfusion of the organ for transplantation, taking a second tissue sample from the organ for transplantation at second timing after the first timing in the reperfusion, measuring contents of the marker substances in the first tissue sample, measuring contents of the marker substances in the second tissue sample, calculating change in content at the second timing as compared with the first timing for each of the marker substances, and calculating an indicator relating to evaluation of the function of the organ for transplantation using the calculated change in content and the data.

Advantageous Effects of Invention

According to the present invention, an indicator for objectively evaluating transplantability of an organ for transplantation can be provided.

BRIEF DESCRIPTION OF DRAWINGS

FIG. 2 is a diagram schematically showing an exemplary configuration of a perfusion circuit.

FIG. 4 is a diagram for illustrating an evaluation criterion in first evaluation.

FIG. 6 is a diagram for illustrating an evaluation criterion in second evaluation.

FIG. 7 is a flowchart for illustrating a method of evaluating a function of a liver graft according to the present embodiment.

DESCRIPTION OF EMBODIMENTS

Figure 1:
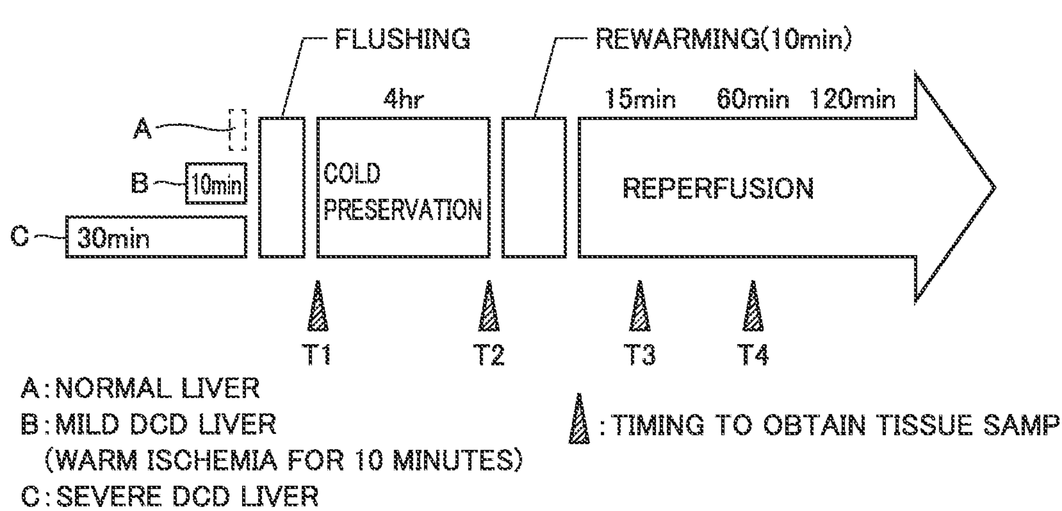
FIG. 1 is a diagram for illustrating a procedure of processing from harvest of liver until reperfusion and timing to obtain a tissue sample.

An embodiment of the present invention will be described in detail below with reference to the drawings. The same or corresponding elements in the drawings below have the same reference characters allotted and description thereof will not be repeated in principle.

Overview of Method of Evaluating Function of Organ for Transplantation

In summary, a method of evaluating a function of an organ for transplantation according to the present embodiment is a method of determining whether or not an organ for transplantation is transplantable by obtaining quantitative data on a marker substance designated in advance by mass spectrometry of the organ for transplantation and evaluating the obtained quantitative data under an evaluation criterion set in advance.

The evaluation criterion used in the method of evaluating the function according to the present embodiment will initially be described below. In succession, the method of evaluating the function based on the evaluation criterion will be described.

A rat is herein employed as a mammal to be a donor of an organ. Liver is adopted as the organ for transplantation. The mammal can be selected as appropriate in accordance with a recipient which is a target to which an organ is transplanted, and for example, human, swine, bovine, apes, dogs, and cats other than rats are applicable. This is because metabolomics analysis is used for obtaining quantitative data of a marker substance. Among omics analyses, metabolomics analysis aims at analysis of a low-molecular weight metabolite. It has already been known that there is no specific difference among low-molecular weight metabolites, there is also a pathway common to substantially all organisms among metabolic pathways such as glycolysis, and results in trials of animals such as rats are readily extrapolated to researches on other species such as human (see, for example, Aono, R. et al., "A pentose bisphosphate pathway for nucleoside degradation in Archaea," Nature Chemical Biology, 11(5), 355-360 (2015) and Yoshida et al., "Metaboromu Kaiseki ni yoru Shoukaki Gan no Shindan—Metaboromikusu ni yoru Suigan Baiomaka Tansaku—(Diagnosis of Digestive Organ Cancer by Metabolomics Analysis—Pancreas Cancer Biomarker Search by Metabolomics)—," The Official Journal of Japanese Society of Laboratory Medicine, 63 (4): 450-456). Organs such as heart, kidney, lung, pancreas, stomach, small intestine, large intestine, testicle, ovary, and eyeball are applicable other than the liver.

(1) Liver Function Evaluation Criterion

In order to create evaluation criteria for functions of liver for transplantation (which is also referred to as a liver graft below), the inventors of the present application conducted perfusion under conditions common to three types of liver different in state of a liver function and measured contents of metabolites contained in each liver by mass spectrometry. In measurement, in order to know how the contents of the metabolites change in a process from after harvest of the liver until reperfusion, a tissue sample was taken at a plurality of timings and mass spectrometry was conducted.

FIG. 1 is a diagram for illustrating a procedure of processing from harvest of liver until reperfusion and timing to obtain a tissue sample.

(1-1) Taking of Tissue Sample

Liver harvested from a Wistar rat was employed as a sample. In the example in FIG. 1, normal liver harvested from a living body of the Wistar rat was adopted as a sample A.

Liver from a donor after circulatory death (DCD) was employed as a sample B. A warm ischemia model was prepared by causing cardiac arrest of a Wistar rat and leaving the Wistar rat at rest for ten minutes, and liver harvested from the prepared warm ischemia model was adopted as sample B.

Liver from a donor after circulatory death (DCD) was employed as a sample C. A warm ischemia model rat was prepared by causing cardiac arrest of a Wistar rat and leaving the Wistar rat at rest for thirty minutes, and liver harvested from the prepared warm ischemia model rat was adopted as sample C. Five samples A, five samples B, and five samples C were prepared.

In harvesting the liver, a perfusate flow-in cannula was inserted in the portal vein of the liver, a perfusate flow-out cannula was inserted in a vein of the liver, and a bile flow-out cannula was inserted in a bile duct. While the cannulas were fixed to the liver, the liver was harvested from the Wistar rat and the harvested liver was accommodated in a storage container.

Sample B and sample C were different from each other in time period from cardiac arrest until harvest of the liver. This time period was regarded as a time period of "warm ischemia" during which blood stream to the liver remained stopped. In the liver in a warm ischemia state, swelling disorder of cells or accumulation of waste products occurred due to exhaustion of adenosine triphosphate (ATP). Therefore, when transplantation was completed and blood stream in the liver was resumed, abrupt metabolism of waste products was caused by an oxygenated perfusate, which might lead to production of a large amount of active oxygen and consequent liver damage. Therefore, in conventional liver transplantation, liver was determined as not being transplantable when the warm ischemia state continued for several minutes. Determination as to transplantability is exclusively based on experiences of a transplantation surgeon and histopathological knowledge. Normally, the liver the warm ischemia state of which has continued for ten minutes is determined as being transplantable, whereas the liver the warm ischemia state of which has continued for thirty minutes is determined as not being transplantable.

In the description below, liver from a donor after circulatory death the warm ischemia state of which has continued for ten minutes is also referred to as "mild DCD liver (mild DCD)." Liver from a donor after circulatory death the warm ischemia state of which has continued for thirty minutes is also referred to as "severe DCD liver (severe DCD)." In the present embodiment, sample A (normal liver) and sample B (mild DCD liver) fall under liver normal in function. Sample C (severe DCD liver) falls under liver poor in function.

Each of samples A to C was then subjected to cleaning (flushing) of the inside of blood vessels in the liver. Physiological saline was used for cleaning. Physiological saline was fed through the perfusate flow-in cannula and drained through the perfusate flow-out cannula. Drained physiological saline was collected without being circulated to the perfusate flow-in cannula.

Then, the cleaned liver was fed with a University of Wisconsin solution (UW solution) to substitute blood with the UW solution, and thereafter the liver was cold-preserved for four hours as being immersed in the UW solution. Cold preservation is on the assumption that a liver graft harvested from a donor is transported to a recipient in an actual medical setting. A time period for cold preservation was set to four hours based on estimation of the longest time period required for transportation. Four hours was set in consideration of use of a liver graft at a remote location.

A temperature of the liver was set back approximately to a body temperature (approximately 37° C.) of the Wistar rat by rewarming the liver after end of cold preservation. Rewarming was carried out for ten minutes.

Figure 2:
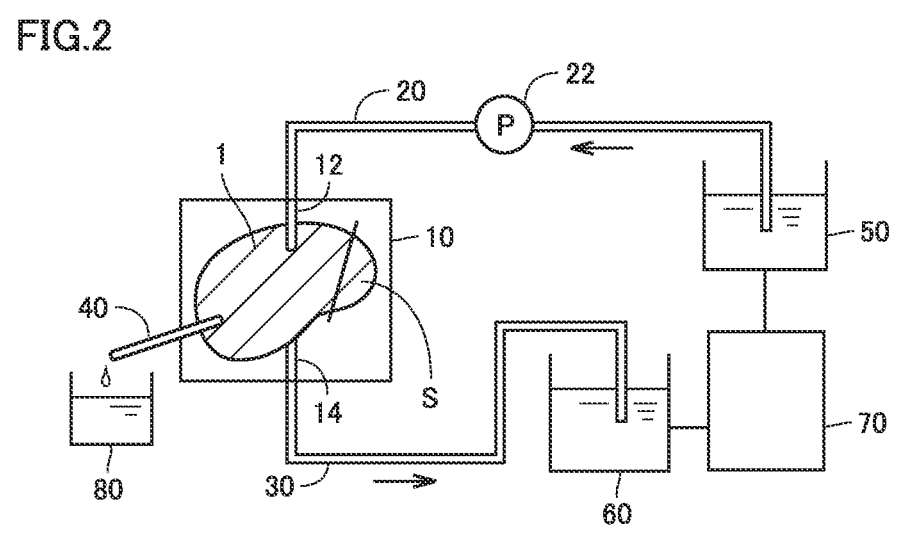

Then, reperfusion of the liver was carried out while the temperature of the liver was maintained at 37° C. Krebs buffer solution was employed as the perfusate. FIG. 2 is a diagram schematically showing an exemplary configuration of a perfusion circuit. Referring to FIG. 2, the perfusion circuit includes a storage container 10, perfusate reservoirs 50 and 60, a perfusate flow-in pathway 20, a perfusate flow-out pathway 30, a gas exchange mechanism 70, and a pump 22.

Liver 1 which is a sample is accommodated in storage container 10. Perfusate reservoirs 50 and 60 are containers where a perfusate is stored. A not-shown temperature mechanism is connected to perfusate reservoirs 50 and 60. The temperature mechanism is configured to keep a perfusate stored in perfusate reservoirs 50 and 60 at a constant temperature (approximately 37° C.).

Perfusate flow-in pathway 20 is connected to a perfusate flow-in cannula 12 provided in storage container 10. Pump 22 is inserted in perfusate flow-in pathway 20. Perfusate flow-out pathway 30 is connected to a perfusate flow-out cannula 14 provided in container 10.

Pump 22 supplies the perfusate to liver 1 through perfusate flow-in pathway 20 from perfusate reservoir 50 via perfusate flow-in cannula 12. At this time, a not-shown controller controls pump 22 such that a pressure of the perfusate is set to 3 to 8 mmHg.

The perfusate that flows out of liver 1 is collected in perfusate reservoir 60 through perfusate flow-out cannula 14 and perfusate flow-out pathway 30. Gas exchange mechanism 70 is configured to dissolve gas such as oxygen by supplying the gas to the perfusate stored in perfusate reservoir 60 and thereafter feed the perfusate back to perfusate reservoir 50.

Though FIG. 2 shows an exemplary configuration of a circulatory perfusion circuit that circulates a perfusate, the perfusion circuit may be configured to collect a used perfusate without circulating the same. Bile provided from the bile duct of liver 1 during reperfusion is collected in a container 80 through a bile flow-out cannula 40.

While a series of steps described above is being performed, a tissue sample S was taken for each sample by cutting a tissue fragment from liver 1. FIG. 1 shows timings T1 to T4 to take a tissue sample.

Timing T1 is set to timing after cleaning of the liver and before cold preservation. Timing T2 is set to timing immediately after cold preservation. In other words, timings T1 and T2 are set before and after cold preservation, respectively.

Timing T3 is set to an initial stage of reperfusion. The initial stage of reperfusion refers to a period during which the liver function is being recovered. In the example in FIG. 1, timing T3 is set to timing fifteen minutes after start of reperfusion.

Timing T4 is set in a latter stage of reperfusion. The latter stage of reperfusion refers to a period during which recovery of the liver function attains to a peak. In the example in FIG. 1, timing T4 is set to timing sixty minutes after start of reperfusion. In other words, timings T3 and T4 are set to timings during reperfusion different in state of the liver function from each other.

(1-2) Mass Spectrometry of Tissue Sample

The tissue samples of samples A to C taken at each of timings T1 to T4 described above were screened by using mass spectrometry. Liquid chromatograph mass spectrometry (LC/MS) was used for mass spectrometry.

Specifically, 500 μL of an internal standard solution was added to the tissue sample (approximately 50 mg) and the resultant sample was homogenized by using BioMasher® (Nippi. Inc.). Then, 250 μL of water was added to this homogenate and the resultant homogenate was agitated. Furthermore, 500 μL of chloroform was added to the homogenate and the resultant homogenate was agitated. After centrifuge (15,000 rpm, 4° C., five minutes), 500 μL of an upper layer was extracted. The extracted solution was dried by using a centrifugal evaporator, and the residue was dissolved again in 50 μL of water. This solution was adopted as a measurement sample.

LC/MS analysis was conducted by using LCMS-8060 (Shimadzu Corporation). Multiple reaction monitoring (MRM) and scan analysis were employed as measurement modes in LC/MS analysis.

Figure 3:
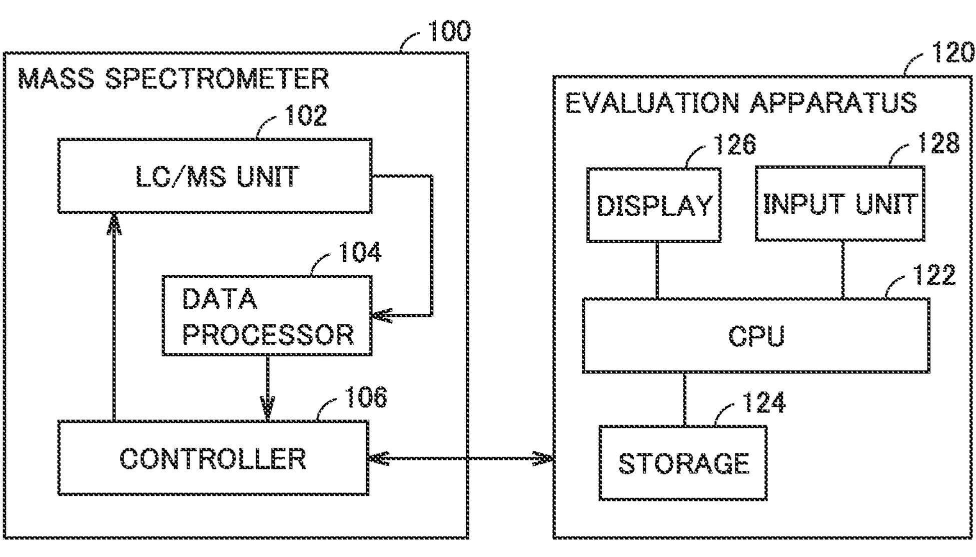
FIG. 3 is a schematic diagram of a configuration of a mass spectrometer and an evaluation apparatus.

FIG. 3 is a schematic diagram of a configuration of a mass spectrometer 100 and an evaluation apparatus 120. Referring to FIG. 3, mass spectrometer 100 includes a liquid chromatograph mass spectrometry (LC/MS) unit 102, a data processor 104, and a controller 106.

LC/MS unit 102 includes a liquid chromatograph including a column (not shown) and a mass spectrometry unit. A sample supplied to the column is separated for each sample component as it passes through the column, successively guided to the mass spectrometry unit in vacuum, and subjected to mass spectrometry. Spectra different depending on a retention time are thus obtained.

The mass spectrometry unit includes, for example, an ionization chamber, an ion trap, and a time of flight mass spectrometer (TOFMS). The ionization chamber ionizes a sample component separated by the liquid chromatograph by using such an ionization method as electrospray ionization (ESI). The method of ionizing a sample component is not limited to ESI and various methods such as atmospheric pressure chemical ionization (APCI) can be employed.

The ion trap is, for example, a three-dimensional quadrupole ion trap, and it can capture ions obtained in the ionization chamber while leaving some of captured ions selectively in the ion trap and cleave the ions by collision induced dissociation (CID). Cleaved ions are supplied from the ion trap to the TOFMS.

In the TOFMS, ions accelerated by electric field formed in a flight space are temporally separated in accordance with a mass-to-charge ratio during their flight in the flight space and successively detected by an ion detector. A detection signal from the ion detector is provided to data processor 104 where it is converted to digital data, and thereafter various types of data processing such as creation of a mass spectrum, a mass chromatogram, or a total chromatogram are performed.

Controller 106 controls operations of LC/MS unit 102. Functions of data processor 104 and controller 106 can be implemented by a personal computer on which prescribed control and processing software has been mounted.

Though a configuration in which a liquid chromatograph mass spectrometer is employed as mass spectrometer 100 is described in the present embodiment, a mass spectrometer including a probe electrospray ionization (PEST) ion source based on PESI (PESI ionization mass spectrometer can also be employed.

Controller 106 transfers data created by data processor 104 to evaluation apparatus 120. Evaluation apparatus 120 is communicatively connected to mass spectrometer 100. Communication between mass spectrometer 100 and evaluation apparatus 120 may be established as wireless communication or wired communication.

Evaluation apparatus 120 includes as its main constituent elements, a central processing unit (CPU) 122 which is a computing unit, a storage 124, a display 126, and an input unit 128. For example, a personal computer can be employed as evaluation apparatus 120.

CPU 122 controls operations of each unit of evaluation apparatus 120 by reading and executing a program stored in storage 124. Specifically, CPU 122 evaluates a function of liver for transplantation which will be described later by executing the program. Though FIG. 3 illustrates a configuration in which a single CPU 122 is provided, evaluation apparatus 120 may include a plurality of CPUs.

Storage 124 is implemented by a non-volatile memory such as a random access memory (RAM), a read only memory (ROM), and a flash memory. A program to be executed by CPU 122 or data to be used by CPU 122 is stored in storage 124. The program may be stored in a non-transitory computer readable medium.

Display 126 and input unit 128 are connected to CPU 122. Display 126 is implemented by a liquid crystal panel or the like on which an image can be shown. Input unit 128 accepts an operation input to evaluation apparatus 120 provided by a user. Input unit 128 is implemented typically by a touch panel, a keyboard, and/or a mouse.

When evaluation apparatus 120 obtains mass spectrum data of the tissue sample of each of samples A to Cat each of timings T1 to T4, the evaluation apparatus conducts quantitative analysis of metabolites contained in the sample based on the obtained mass spectrum data. An evaluation criterion to be used for evaluation of a function of a liver graft is set by using quantitative data obtained at this time.

(1-3) Setting of Evaluation Criterion

The method of evaluating the liver function according to the present embodiment is composed of evaluation in two stages. First evaluation is made by using quantitative data obtained before reperfusion, and in the first evaluation, whether or not the function of the liver graft is satisfactory is evaluated. Second evaluation is made by using quantitative data obtained during reperfusion, and in the second evaluation, whether or not the liver graft, the function of which has been maintained or recovered by reperfusion, is transplantable is evaluated. Since the first evaluation is preliminary evaluation for final second evaluation, it does not have to be made.

(i) Evaluation Criterion in First Evaluation

In the first evaluation, a marker substance for evaluating the liver function and a threshold value for determining whether or not the liver function is satisfactory were employed as evaluation criteria. Then, a marker substance was identified based on quantitative data of three types of samples A to C described above and the threshold value was set for each marker substance.

Specifically, a marker substance candidate was identified based on quantitative data of samples A to C taken at each of timings T1 and T2 from a point of view that the liver graft normal in function exhibited a large numeric value and the liver graft poor in function exhibited a small numeric value.

In the quantitative data at timing T1 which was before cold preservation, two metabolites were identified as the marker substance candidates that exhibited large numeric values in sample A (normal liver) and sample B (mild DCD liver) and exhibited a small numeric value in sample C (severe DCD liver). The two metabolites are uridine and adenylosuccinic acid.

In the quantitative data at timing T2 which was after cold preservation, one metabolite was identified as the marker substance candidate that exhibited large numeric values in sample A (normal liver) and sample B (mild DCD liver) and exhibited a small numeric value in sample C (severe DCD liver). This metabolite is uridine.

FIG. 4 shows a content of a marker substance in quantitative data at timing T1 and a content of the marker substance in quantitative data at timing T2. FIG. 4 (A) shows a graph of the content of uridine at timing T1 in each of samples A to C and FIG. 4 (B) shows a graph of the content of adenylosuccinic acid at timing T1 in each of samples A to C. The ordinate in each graph corresponds to a value (a peak area ratio of a mass spectrum/an amount of protein) calculated by dividing a peak area ratio of a mass spectrum by an amount of protein. The peak area ratio of the mass spectrum refers to a ratio of a peak area of a target component to a peak area of an internal standard reference material. The amount of protein is measured by quantitative analysis of an amount of protein for each tissue sample.

In the graph in FIG. 4 (A), at timing T1, the content of uridine decreases in the order of the normal liver, the mild DCD liver, and the severe DCD liver. Then, a threshold value U1 for determining whether or not the liver function was satisfactory was set between the normal liver and the mild DCD liver, and the severe DCD liver. Specifically, an average value of an average value of the contents of uridine in the normal liver and the mild DCD liver and an average value of the contents of uridine in the severe DCD liver was set as threshold value U1.

As shown in the graph in FIG. 4 (B), at timing T1, the content of adenylosuccinic acid decreases in the order of the normal liver, the mild DCD liver, and the severe DCD liver. Then, a threshold value A1 for determining whether or not the liver function was satisfactory was set between the normal liver and the mild DCD liver, and the severe DCD liver. Specifically, an average value of an average value of the contents of adenylosuccinic acid in the normal liver and the mild DCD liver and an average value of the contents of adenylosuccinic acid in the severe DCD liver was set as threshold value A1.

As shown in the graph in FIG. 4 (C), at timing T2, the content of uridine decreases in the order of the normal liver, the mild DCD liver, and the severe DCD liver. Then, a threshold value U2 for determining whether or not the liver function was satisfactory was set between the normal liver and the mild DCD liver, and the severe DCD liver. Specifically, an average value of an average value of the contents of uridine in the normal liver and the mild DCD liver and an average value of the contents of uridine in the severe DCD liver was set as threshold value U2.

(ii) Evaluation Criterion in Second Evaluation

In the second evaluation, a marker substance for evaluating the liver function maintained and recovered by reperfusion and a threshold value for determining transplantability were employed as evaluation criteria. Then, a marker substance was identified based on quantitative data of three types of samples A to C described above and a threshold value was set for each marker substance.

Specifically, a marker substance candidate was identified based on the quantitative data of samples A to C taken at each of timings T3 and T4 from a point of view of change in content during reperfusion. Ten metabolites were identified as the marker substance candidates changed in content between timing T3 and timing T4. The ten metabolites were sedoheptulose 7-phosphate, adenosine triphosphate, glucose-6-phosphate, succinyl coenzyme A (CoA), dimethylglycine, choline, 2-aminobutyric acid, uric acid, pyruvic acid, and inosine.

Figure 5:
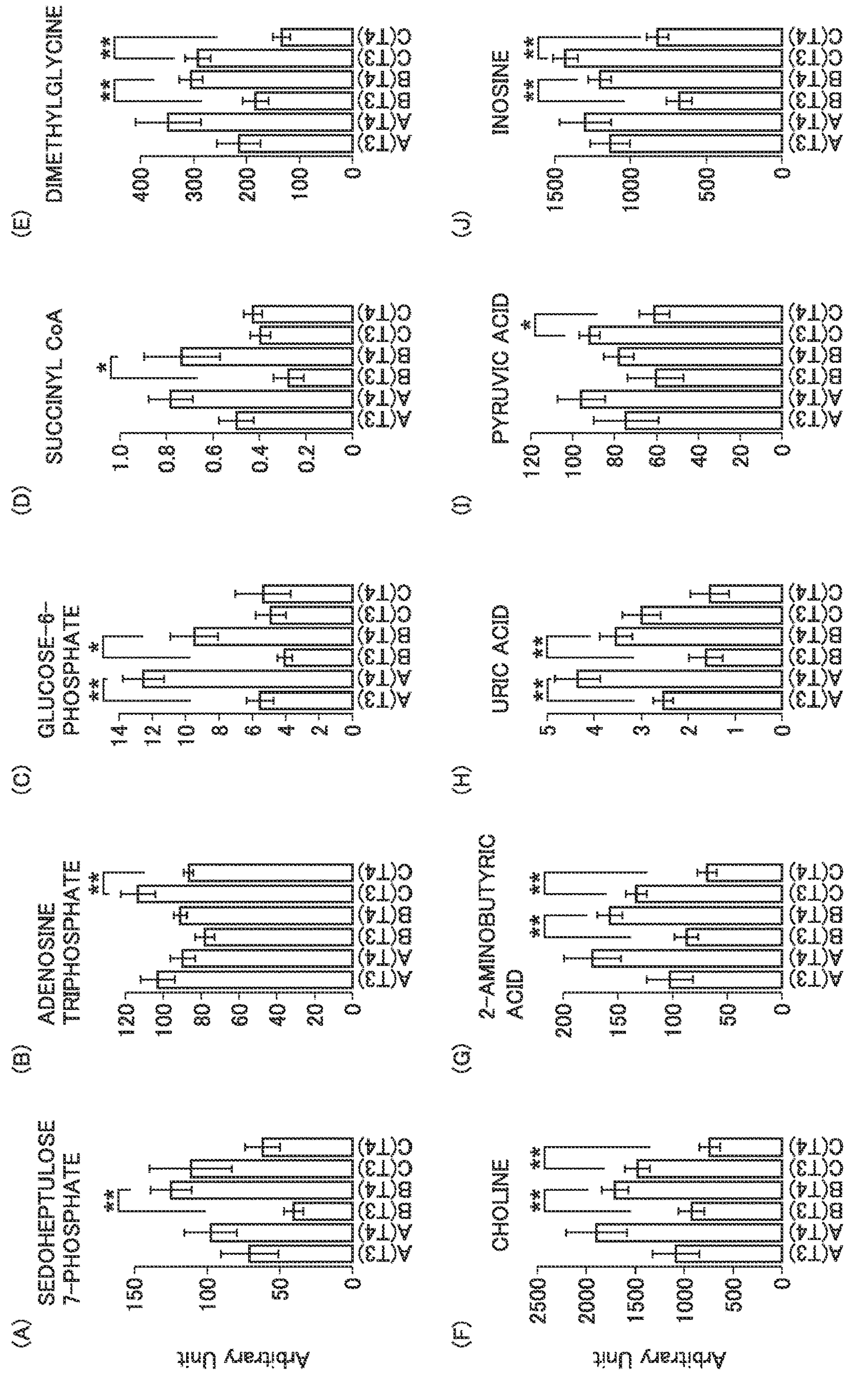
FIG. 5 is a diagram for illustrating an evaluation criterion in second evaluation.

FIG. 5 shows contents of the marker substances in quantitative data at timing T3 and contents of the marker substances in quantitative data at timing T4. FIG. 5 (A) to (J) show graphs of the contents of the marker substances at timings T3 and T4 of each of samples A to C.

In each figure, A(T3) represents the content of the marker substance at timing T3 in sample A (normal liver) and A(T4) represents the content of the marker substance at timing T4 in sample A (normal liver). B(T3) represents the content of the marker substance at timing T3 in sample B (mild DCD liver) and B(T4) represents the content of the marker substance at timing T4 in sample B (mild DCD liver). C(T3) represents the content of the marker substance at timing T3 in sample C (severe DCD liver) and C(T4) represents the content of the marker substance at timing T4 in sample C (severe DCD liver). The ordinate in each graph corresponds to a value (a peak area ratio of a mass spectrum/an amount of protein) calculated by dividing a peak area ratio of a mass spectrum by an amount of protein.

As shown in FIG. 5 (A), the content of sedoheptulose 7-phosphate increases in the normal liver and the mild DCD liver and decreases in severe DCD liver. As shown in FIGS. 5 (E), (F), (G), (H), (I), and (J), the contents of dimethylglycine, choline, 2-aminobutyric acid, uric acid, pyruvic acid, and inosine also exhibited a tendency similar to that of sedoheptulose 7-phosphate.

In contrast, as shown in FIG. 5 (B), the content of adenosine triphosphate decreases in the normal liver, increases in the mild DCD liver, and decreases in the severe DCD liver. As shown in FIGS. 5 (C) and (D), the contents of glucose-6-phosphate and succinyl CoA increase in all of the normal liver, the mild DCD liver, and the severe DCD liver.

FIG. 6 collectively shows tendencies of change in content of the ten marker substances shown in FIG. 5 from timing T3 to timing T4. FIG. 6 shows a table showing with scores, the tendency of change in content in five samples in total for each of samples A to C. In this table, for each marker substance, increase in content from timing T3 to timing T4 was expressed as a score "1" and decrease in content was expressed as a score "0".

Increase/decrease in content may be determined based on difference in content between timings T3 and T4. In this case, the content higher at timing T4 than at timing T3 is expressed as the score "1" and the content lower at timing T4 than at timing T3 is expressed as the score "0".

Alternatively, increase/decrease in content may be determined based on a rate of change in content between timings T3 and T4. In this case, a ratio of the content at timing T4 to the content at timing T3 is calculated. When the content is equal between timings T3 and T4, a condition of the ratio=1 is satisfied. When the content at timing T4 is higher than the content at timing T3, a condition of the ratio >1 is satisfied, and when the content at timing T4 is lower than the content at timing T3, a condition of the ratio <1 is satisfied.

A first threshold value larger than one and a second threshold value smaller than one are set in advance for the ratio, and the calculated ratio is compared with the first and second threshold values. When the calculated ratio is higher than the first threshold value, determination as increase in content is made and the score is set to "1". When the calculated ratio is lower than the second threshold value, determination as decrease in content is made and the score is set to "0".

Referring to FIG. 6, for example, in the case of sedoheptulose 7-phosphate, in sample A (normal liver), two samples A1 and A3 of five samples A1 to A5 exhibited the score "1" and three remaining samples A2, A4, and A5 exhibited the score "0". In contrast, in sample B (mild DCD liver), all of five samples B1 to B5 exhibited the score "1", and in sample C (severe DCD liver), all of five samples C1 to C5 exhibited the score "0".

In the case of glucose-6-phosphate, dimethylglycine, choline, 2-aminobutyric acid, and uric acid, in sample A (normal liver) and sample B (mild DCD liver), all of the five samples exhibited the score "1", and in sample C (severe DCD liver), all of five samples C1 to C5 exhibited the score "0".

After the score was calculated for each marker substance, a total value of the ten scores was calculated for each sample. Specifically, a largest value of the total score was "10" and a smallest value was "0".

As shown in FIG. 6, the total scores of sample A (normal liver) and sample B (mild DCD liver) are distributed around the largest value "10". In contrast, the total scores of sample C (severe DCD liver) are distributed around the smallest value "0".

According to the table in FIG. 6, in nine of the ten marker substances, sample A (normal liver) and sample B (mild DCD liver) agree with each other in tendency of change in content of the marker substances from timing T3 to timing T4. Consequently, the normal liver and the mild DCD liver are close to each other in total score.

In contrast, in nine of the ten marker substances, sample A (normal liver) is different from sample C (severe DCD liver) in tendency of change in content of the marker substances from timing T3 to timing T4. Consequently, the normal liver and the severe DCD liver are not close to each other in total score but different in value thereof. In the table in FIG. 6, the severe DCD liver is significantly smaller in total score than the normal liver.

The inventors of the present application set based on the table in FIG. 6, a threshold value for separating the normal liver and the mild DCD liver from the severe DCD liver in terms of the total score, and set this threshold value as a reference value for determining whether a liver graft is a liver graft the function of which has been recovered by reperfusion or a liver graft the function of which has not been recovered.

Specifically, the reference value was set to "2" because the total scores of the normal liver and the mild DCD liver were each in a range from "6" to "10" whereas the total score of the severe DCD liver was "0" or "1".

Thus, whether or not the reperfused liver graft is transplantable can be determined based on the total score. Specifically, when the total score of the liver graft is larger than the reference value "2", the liver graft is determined as being transplantable. In this case, it can be determined that the liver graft agrees with the normal liver in tendency of change in content of the marker substances from timing T3 to timing T4. Therefore, it can be determined that the function of the liver graft was recovered to a transplantable level by reperfusion.

When the total score of the liver graft is equal to or smaller than the threshold value "2", the liver graft is determined as not being transplantable. In this case, it can be determined that the liver graft is different from the normal liver in tendency of change in content of the marker substances from timing T3 to timing T4. Therefore, it can be determined that the function of the liver graft has not been recovered to the transplantable level even by reperfusion.

In the second evaluation, transplantability is determined based on the total score of scores of the ten marker substances, so that variation in score among the marker substances can be accommodated. In other words, even for the normal liver, tendencies of increase/decrease in content are varied among a plurality of samples. Therefore, in determining whether or not the tendency of change in content agrees with that of the normal liver for each marker substance, erroneous determination may be made. Such erroneous determination can be prevented by comprehensively determining whether or not the tendency of change in content agrees in all marker substances based on the total score of the all marker substances.

(2) Method of Evaluating Liver Function

A method of evaluating a function of a liver graft based on the evaluation criteria described above will now be described.

FIG. 7 is a flowchart for illustrating a method of evaluating a function of a liver graft according to the present embodiment. FIG. 7 shows a flowchart (left in FIG. 7) illustrating a procedure of processing from harvest of the liver graft until reperfusion, a flowchart (center in FIG. 7) illustrating a procedure of processing in the mass spectrometer, and a flowchart (right in FIG. 7) illustrating a procedure of processing in the evaluation apparatus.

Referring to FIG. 7, in step S10, a liver graft is harvested from a donor. In step S20, flushing processing for cleaning blood vessels in the harvested liver graft is performed. For example, physiological saline can be used for cleaning. The cleaned liver graft is immersed in the UW solution.

In step S30, a tissue sample is taken from the liver graft. Taking of the tissue sample in step S30 corresponds to timing T1 in FIG. 1.

In step S40, processing for cold preservation of the liver graft is performed. A time period for cold preservation is not particularly limited, and a user can set as appropriate the time period in consideration of a time period for transportation of the liver graft from a donor to a recipient. A preservation medium is not limited to the UW solution and the user can select the preservation medium as appropriate.

At the time point of end of cold preservation processing (step S40), in step S50, a tissue sample is taken from the liver graft. Taking of the tissue sample in step S50 corresponds to timing T2 in FIG. 1.

In step S60, processing for rewarming the liver graft is performed. The temperature of the liver graft is set back to approximately 37° C. by rewarming processing.

In step S70, processing for reperfusing the liver graft is performed while the temperature of the liver graft is maintained at approximately 37° C. The reperfusion processing can be performed, for example, by using the perfusion circuit shown in FIG. 2. The perfusate is not limited to the Krebs buffer solution but a user can select as appropriate the perfusate.

When reperfusion is started, in step S80, a tissue sample is taken from the liver graft at prescribed timing in the initial stage of reperfusion (for example, fifteen minutes after start of reperfusion). Taking of the tissue sample in step S80 corresponds to timing T3 in FIG. 1. In step S90, at prescribed timing in termination of reperfusion (for example, thirty minutes after start of reperfusion), a tissue sample is taken from the liver graft. Taking of the tissue sample in step S90 corresponds to timing T4 in FIG. 1.

In step S31, mass spectrometry of the tissue sample taken in step S30 is conducted in mass spectrometer 100. Mass spectrum data obtained in this mass spectrometry is transferred to evaluation apparatus 120.

Thereafter, in steps S51, S81, and S91, mass spectrometry of the tissue samples taken in steps S50, S80, and S90 is conducted in mass spectrometer 100. Mass spectrum data obtained in mass spectrometry processing is transferred to evaluation apparatus 120.

In evaluation apparatus 120, whether or not the liver graft is transplantable is evaluated based on the mass spectrum data transferred from mass spectrometer 100.

Specifically, initially, in S32, evaluation apparatus 120 obtains mass spectrum data of the tissue sample taken at timing T1 before cold preservation (S40), and in succession in step S52, evaluation apparatus 120 obtains mass spectrum data of the tissue sample taken at timing T2 after cold preservation (S40). In step S100, evaluation apparatus 120 performs first evaluation processing by using these two pieces of mass spectrum data.

Figure 8:
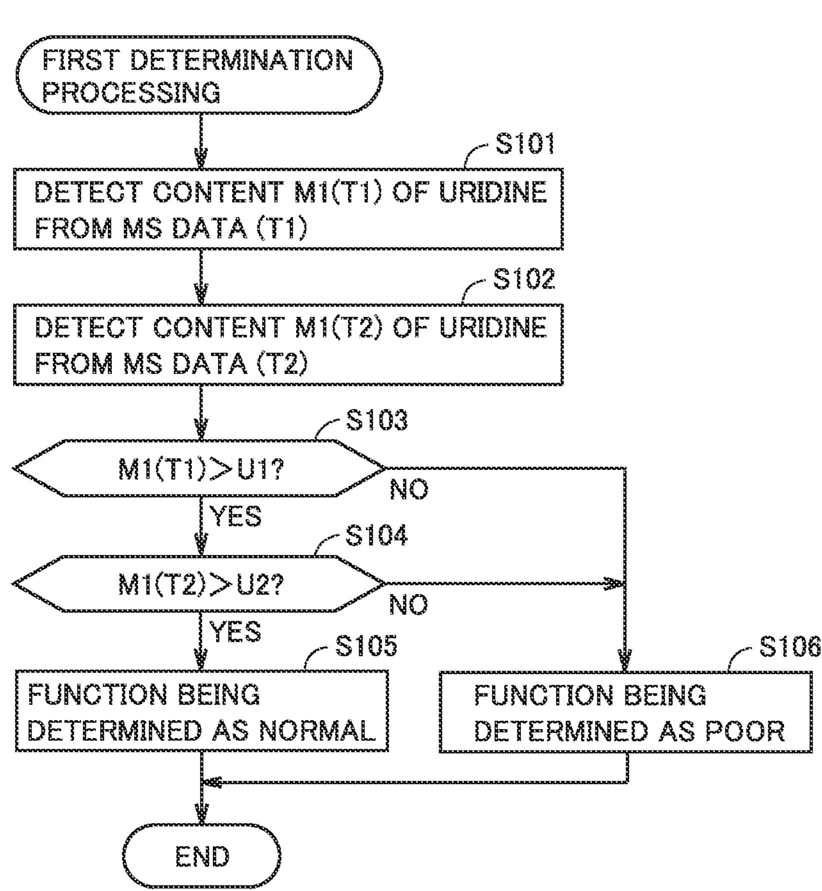
FIG. 8 is a flowchart for illustrating a procedure in first evaluation processing shown in step S100 in FIG. 7.

FIG. 8 is a flowchart for illustrating a procedure in the first evaluation processing shown in step S100 in FIG. 7. The flowchart in FIG. 8 can be performed by CPU 122 of evaluation apparatus 120.

Referring to FIG. 8, in step S101, CPU 122 detects a content M1(T1) of uridine representing the marker substance from mass spectrum data at timing T1. In succession, in step S102, CPU 122 detects a content M1(T2) of uridine from mass spectrum data at timing T2. In steps S101 and S102, CPU 122 detects content M1 of uridine by dividing the peak area ratio of the mass spectrum by the amount of protein.

Then, in step S103, CPU 122 compares content M1(T1) of uridine with threshold value U1. Threshold value U1 is set based on the content of uridine in the normal liver, the mild DCD liver, and the severe DCD liver at timing T1 in FIG. 4 (A).

When content M1(T1) of uridine is equal to or lower than threshold value U1 (NO in S103), in step S106, CPU 122 determines the liver graft as being poor in function.

When M1 (T1) content is higher than threshold value U1 (YES in S103), in succession in step S104, CPU 122 compares content M1 (T2) of uridine with threshold value U2. Threshold value U2 is set based on the content of uridine in the normal liver, the mild DCD liver, and the severe DCD liver at timing T2 in FIG. 4 (C).

When content M1(T2) of uridine is equal to or lower than threshold value U2 (NO in S104), in step S106, CPU 122 determines the liver graft as being poor in function. When content M1(T2) of uridine is higher than threshold value U2 (YES in S104), in step S105, CPU 122 determines the liver graft as being normal in function.

Figure 9:
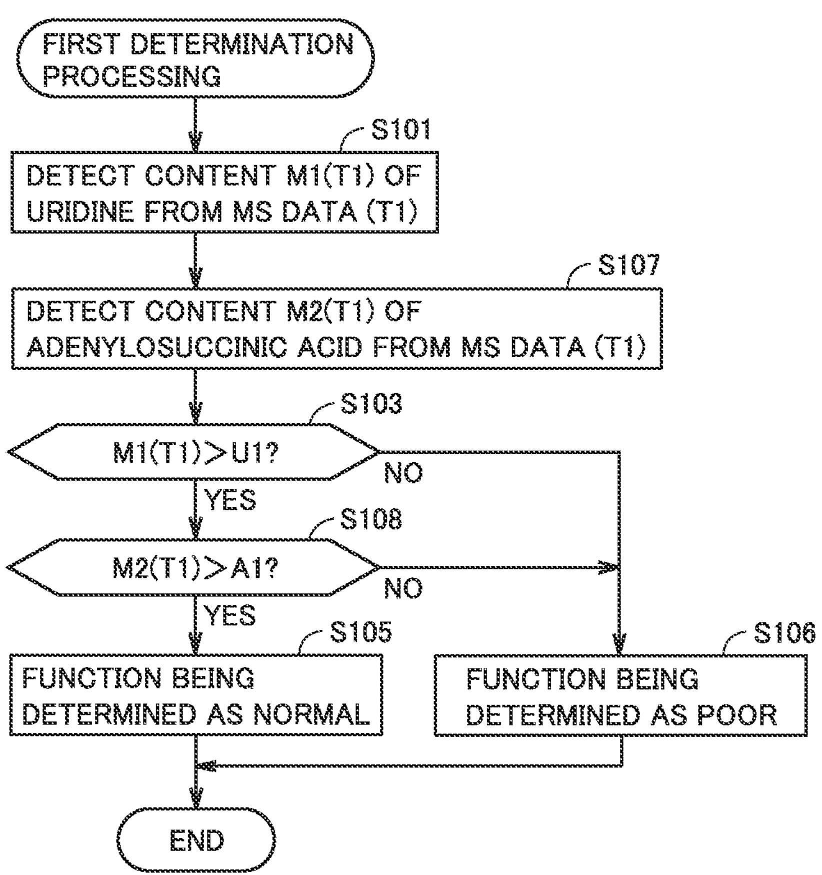
FIG. 9 is a flowchart for illustrating a first modification of the first evaluation processing shown in step S100 in FIG. 7.
Figure 10:
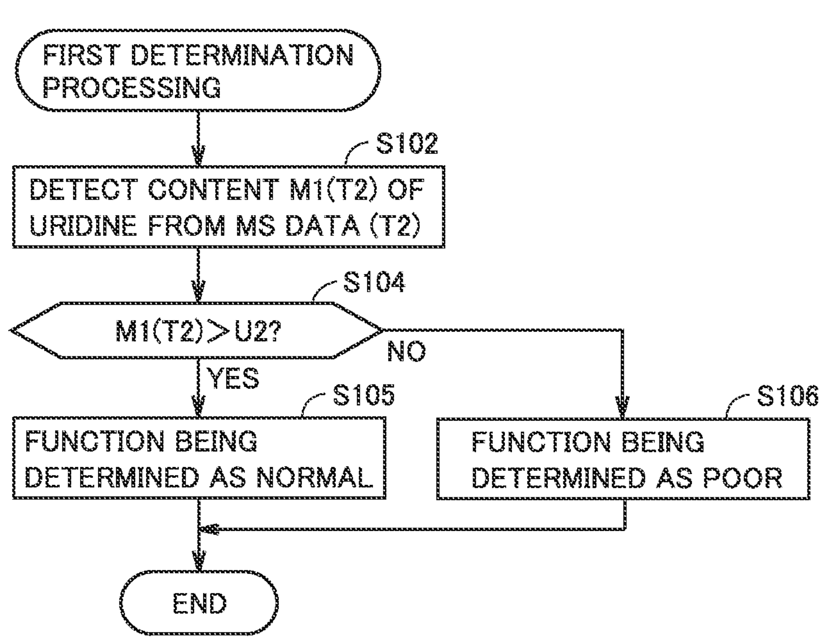
FIG. 10 is a flowchart for illustrating a second modification of the first evaluation processing shown in step S100 in FIG. 7.

Though the function of the liver graft is determined based on the content of uridine at timings T1 and T2 in the flowchart shown in FIG. 8, the function of the liver graft can be determined also based on the contents of uridine and adenylosuccinic acid at timing T1 as shown in FIG. 9. Alternatively, the function of the liver graft can be determined also based on the content of uridine at timing T2 as shown in FIG. 10.

FIG. 9 is a flowchart for illustrating a first modification of the first evaluation processing shown in step S100 in FIG. 7.

Referring to FIG. 9, in step S101, CPU 122 detects content M1(T1) of uridine representing the marker substance from the mass spectrum data at timing T1. In succession in step S107, CPU 122 detects a content M2(T1) of adenylosuccinic acid from the mass spectrum data at timing T1.

Then, in step S103, CPU 122 compares content M1(T1) of uridine with threshold value U1. When content M1(T1) of uridine is equal to or lower than threshold value U1 (NO in S103), in step S106, CPU 122 determines the liver graft as being poor in function.

When content M1(T1) is higher than threshold value U1 (YES in S108), in succession in step S104, CPU 122 compares content M2(T1) of adenylosuccinic acid with threshold value A1. Threshold value A1 is set based on the content of adenylosuccinic acid in the normal liver, the mild DCD liver, and the severe DCD liver at timing Tl in FIG. 4 (B).

When content M2(T1) of adenylosuccinic acid is equal to or lower than threshold value A1 (NO in S108), in step S106, CPU 122 determines the liver graft as being poor in function. When content M2(T1) of adenylosuccinic acid is higher than threshold value A1 (YES in S108), in step S105, CPU 122 determines the liver graft as being normal in function.

FIG. 10 is a flowchart for illustrating a second modification of the first evaluation processing shown in step S100 in FIG. 7.

Referring to FIG. 10, in step S102, CPU 122 detects content M1(T2) of uridine representing the marker substance from the mass spectrum data at timing T2.

Then, in step S104, CPU 122 compares content M1(T2) of uridine with threshold value U2. When content M1(T2) of uridine is equal to or lower than threshold value U2 (NO in S104), in step S106, CPU 122 determines the liver graft as being poor in function. When content M1(T2) is higher than threshold value U2 (YES in S104), in step S105, CPU 122 determines the liver graft as being normal in function.

Referring back to FIG. 7, in step S82, evaluation apparatus 120 obtains mass spectrum data of the tissue sample taken at timing T3 in the initial stage of reperfusion, and in succession in step S92, evaluation apparatus 120 obtains mass spectrum data of the tissue sample taken at timing T4 in the latter stage of reperfusion. In step S200, evaluation apparatus 120 performs second evaluation processing by using these two pieces of mass spectrum data.

Figure 11:
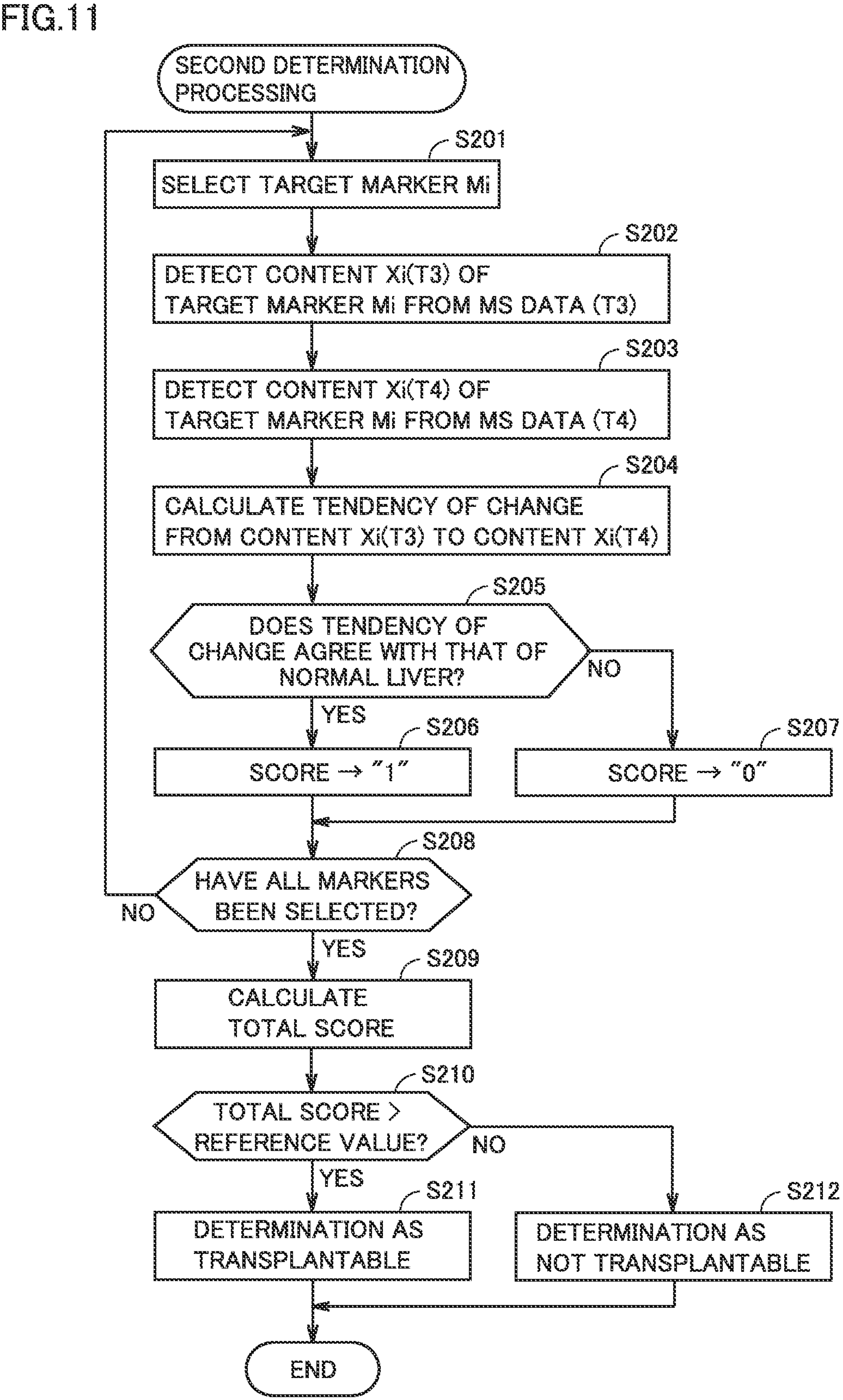
FIG. 11 is a flowchart for illustrating a procedure in second evaluation processing shown in step S200 in FIG. 7.

Referring to FIG. 11, in step S201, CPU 122 selects a target marker substance Mi (i being an integer not smaller than one and not larger than ten) from among ten marker substances. Then, in step S202, CPU 122 detects a content Xi(T3) of a metabolite representing target marker substance Mi from the mass spectrum data at timing T3. In step S203, CPU 122 further detects a content Xi(T4) of target marker substance Mi from the mass spectrum data at timing T4. In steps S202 and S203, CPU 122 detects content Xi of the target marker substance by dividing the peak area ratio of the mass spectrum by the amount of protein.

Then, in step S204, CPU 122 calculates a tendency of change in content Xi from timing T3 to timing T4. In step S204, for example, CPU 122 determines the tendency (increase/decrease) of change in content Xi based on difference between Xi(T3) and Xi(T). In this case, when a condition of Xi (T3) <Xi (T4) is satisfied, CPU 122 determines content Xi as having increased, and when a condition of Xi(T3) >Xi(T4) is satisfied, it determines content Xi as having decreased.

Alternatively, CPU 122 can determine increase/decrease in content Xi based on a rate of change between Xi(T3) and Xi(T4) (=Xi(T4)/Xi(T3)). CPU 122 calculates a ratio of content Xi(T4) to content Xi(T3). When relation of Xi(T3) =Xi(T4) is satisfied, a condition of the ratio=1 is satisfied. When, relation of Xi(T4)>Xi(T3) is satisfied, a condition of the ratio>1 is satisfied, and when relation of Xi(T4)<Xi(T3) is satisfied, a condition of the ratio<1 is satisfied.

CPU 122 compares the calculated rate of change with the first threshold value (the first threshold value>1). When the rate of change is higher than the first threshold value, CPU 122 determines content Xi as having increased. CPU 122 compares the rate of change with the second threshold value (the second threshold value<1). When the rate of change is lower than the second threshold value, CPU 122 determines content Mi as having decreased.

Then, the process proceeds to step S205, and CPU 122 determines whether or not the tendency of change in content Xi found in step S204 agrees with the tendency of change in content of marker substance Mi in the normal liver. The tendency of change in content of marker substance Mi in the normal liver is based on the contents of the marker substance at timings T3 and T4 in the normal liver (sample A) shown in FIG. 5. CPU 122 can calculate the tendency of change in content of marker substance Mi in the normal liver with a method similar to the method described with reference to step S204.

In step S205, when the tendency of change in content of marker substance Mi in the liver graft agrees with the tendency of change in content of marker substance Mi in the normal liver (YES in S205), in step S206, CPU 122 sets the score for marker substance Mi to “1”. When the tendency of change in content of marker substance Mi in the liver graft does not agree with the tendency of change in content of marker substance Mi in the normal liver (NO in S205), in step S207, CPU 122 sets the score for marker substance Mi to “0”.

When the score at the time when the tendency of change in content of marker substance Mi in the liver graft is high in degree of agreement with the tendency of change in content of marker substance Mi in the normal liver is different from the score at the time when the degree of agreement is low, values of the score are not limited to “1” and “0”. An absolute value of change may be calculated, and when the degree of agreement is high, the score may be set to “1”, when the degree of agreement is low, the score may be set to “0”, and when the degree of agreement is intermediate therebetween, the score may be set to “0.5”.

Then, in step S208, CPU 122 determines whether or not all of the ten marker substances have been selected as the target marker substances. When all marker substances have not been selected (NO in S208), the process returns to step S201 and CPU 122 selects a next marker substance M(i+1) as the target marker substance and performs again processing in step S202 to S207.

When all of the ten marker substances have been selected as the target marker substance (YES in S208), the process proceeds to step S209 and CPU 122 calculates the total score by summing the scores of all marker substances.

In step S210, CPU 122 compares the total score calculated in step S209 with the reference value (=2). The reference value is set based on the total score of the normal liver, the mild DCD liver, and the severe DCD liver shown in FIG. 6.

When the total score is larger than the reference value (YES in S210), in step S211, CPU 122 determines the liver graft as being transplantable. When the total score is equal to or smaller than the reference value (NO in S210), in step S212, CPU 122 determines the liver graft as not being transplantable.

In other words, the score or the total score for each marker substance functions as an indicator relating to evaluation of the function of the liver graft.

Referring back to FIG. 7, in step S300, CPU 122 has display 126 show a result of evaluation in the first evaluation processing (S100) and the second evaluation processing (S200). A user such as a transplantation surgeon can determine whether or not to transplant the liver graft to a recipient based on the result of evaluation shown on display 126.

As described above, with the method of evaluating the function of the organ for transplantation according to the present embodiment, whether or not the organ for transplantation is transplantable is determined by obtaining quantitative data of a marker substance designated in advance by mass spectrometry of the organ for transplantation and evaluating the obtained quantitative data in accordance with an evaluation criterion set in advance. According to this method, determination as to transplantability of an organ for transplantation that has conventionally been made based on experiences of a transplantation surgeon and histopathological knowledge can objectively be made. Since transplantability can be determined before transplantation of an organ, organs that can be used for transplantation can be increased.

Furthermore, according to the method of evaluating the function of the organ for transplantation according to the present embodiment, possibility of use of not only brain death liver but also liver from a donor after circulatory death, the function of which has been recovered by reperfusion, can be enhanced, which can contribute to solution of lack of donor organs.

OTHER EMBODIMENTS

The function of an organ for transplantation is evaluated by expressing as a score, a degree of agreement between the tendency of change in content of marker substance Mi in a liver graft and tendency of change in content of marker substance Mi in the normal liver and calculating a total of scores of each marker substance. In another embodiment, the function of an organ for transplantation may be evaluated by regression analysis without using a score. For example, a regression equation may be created by defining an amount of change in content of marker substance Mi as an explanatory variable and defining normality of the function of the organ for transplantation as an objective variable.

ASPECTS

A plurality of illustrative embodiments described above are understood by a person skilled in the art as specific examples of aspects below.

(Clause 1) A method of evaluating a function of an organ for transplantation according to one aspect is a method of evaluating a function of an organ for transplantation harvested from a living body, and the method includes preparing data representing change over time in contents of marker substances in accordance with a perfusion, taking a first tissue sample from the organ for transplantation at first timing in a reperfusion of the organ for transplantation, taking a second tissue sample from the organ for transplantation at second timing after the first timing in the reperfusion, measuring contents of the marker substances in the first tissue sample, measuring contents of the marker substances in the second tissue sample, calculating change in content at the second timing as compared with the first timing for each of the marker substances, and calculating an indicator relating to evaluation of the function of the organ for transplantation using the calculated change in content and the data.

According to the method of evaluating the function described in Clause 1, by expressing change in content of each of marker substances during reperfusion as an indicator, whether or not an organ for transplantation is transplantable can be determined based on the indicator. Thus, whether or not an organ for transplantation is transplantable can objectively be determined before transplantation. Possibility of use for transplantation also of an organ from a donor after circulatory death the function of which has been recovered by reperfusion is enhanced, which can contribute to solution of lack of donor organs.

(Clause 2) In the method of evaluating a function of an organ for transplantation described in Clause 1, the calculating change includes calculating a tendency of change in the content. The calculating an indicator includes expressing the tendency of change in the content as a score. The expressing the tendency as a score includes setting a score at the time when the tendency of change in the content in the organ for transplantation agrees with the tendency of change in the content in an organ normal in function to be larger than a score at the time when the tendency of change in the content in the organ for transplantation does not agree with the tendency of change in the content in the organ normal in function.

According to the method of evaluating the function described in Clause 2, by expressing as a score, the tendency of change in the content of each of the marker substances during reperfusion based on the tendency of change in the content of each of the marker substances in an organ normal in function, transplantability can objectively be determined based on the score.

(Clause 3) In the method of evaluating a function of an organ for transplantation described in Clause 1 or 2, each of the measuring contents of the marker substances in the first tissue sample and the measuring contents of the marker substances in the second tissue sample includes measuring contents of the marker substances by mass spectrometry.

According to the method of evaluating the function described in Clause 3, by mass spectrometry of the first and second tissue samples, change in content of each of the marker substances during reperfusion can be expressed as an indicator.

(Clause 4) In the method of evaluating a function of an organ for transplantation described in Clauses 1 to 3, the calculating change further includes making determination as increase in the content when a rate of change in the content at the second timing as compared with the content at the first timing is higher than a first threshold value larger than one and making determination as decrease in the content when the rate of change is lower than a second threshold value smaller than one.

According to the method of evaluating the function described in Clause 4, change in the content of each of the marker substances during reperfusion can appropriately be expressed as a score regardless of variation among tissue samples. Transplantability can thus highly accurately be determined.

(Clause 5) In the method of evaluating a function of an organ for transplantation described in Clauses 1 to 4, the organ for transplantation is liver. The marker substances include at least two of sedoheptulose 7-phosphate, adenosine triphosphate, glucose-6-phosphate, succinyl coenzyme A (CoA), dimethylglycine, choline, 2-aminobutyric acid, uric acid, pyruvic acid, and inosine.

According to the method of evaluating the function described in Clause 5, by expressing change in the content of each of the marker substances during perfusion as an indicator, whether or not a liver graft is transplantable can be determined based on the indicator. Thus, whether or not a liver graft is transplantable can objectively be determined before transplantation. Possibility of use for transplantation also of liver from a donor after circulatory death the function of which has been recovered by reperfusion is enhanced, which can contribute to solution of lack of donor organs.

(Clause 6) The method of evaluating a function of an organ for transplantation described in Clauses 1 to 5 includes cold-preserving the organ for transplantation after harvesting from a donor until the reperfusion, taking a third tissue sample from the organ for transplantation at third timing before start of cold preservation, taking a fourth tissue sample from the organ for transplantation at fourth timing after end of cold preservation and before start of the reperfusion, measuring a content of a first marker substance in the third tissue sample, measuring a content of the first marker substance in the fourth tissue sample, and determining whether or not the function of the organ for transplantation is normal based on the contents of the first marker substance at the third timing and the fourth timing.

According to the method of evaluating the function described in Clause 6, whether or not the function of the organ for transplantation before perfusion is satisfactory can be determined.

(Clause 7) The method of evaluating a function of an organ for transplantation described in Clauses 1 to 5 includes cold-preserving the organ for transplantation after harvesting from a donor until the reperfusion, taking a fourth tissue sample from the organ for transplantation at fourth timing after end of cold preservation and before start of the reperfusion, measuring a content of a first marker substance in the fourth tissue sample, and determining whether or not the function of the organ for transplantation is normal based on the content of the first marker substance at the fourth timing.

According to the method of evaluating the function described in Clause 7, whether or not the function of the organ for transplantation before reperfusion is satisfactory can be determined.

(Clause 8) The method of evaluating a function of an organ for transplantation described in Clauses 1 to 5 includes cold-preserving the organ for transplantation after harvesting from a donor until the reperfusion, taking a third tissue sample from the organ for transplantation at third timing before start of cold preservation, measuring contents of first and second marker substances in the third tissue sample, and determining whether or not the function of the organ for transplantation is normal based on the contents of the first and second marker substances at the third timing.

According to the method of evaluating the function described in Clause 8, whether or not the function of the organ for transplantation before reperfusion is satisfactory can be determined.

(Clause 9) In the method of evaluating a function of an organ for transplantation described in Clause 6 or 7, the organ for transplantation is liver and the first marker substance is uridine.

According to the method of evaluating the function described in Clause 9, whether or not the function of a liver graft before reperfusion is satisfactory can be determined.

(Clause 10) In the method of evaluating a function of an organ for transplantation described in Clause 8, the organ for transplantation is liver. The first marker substance is uridine and the second marker substance is adenylosuccinic acid.

According to the method of evaluating the function described in Clause 10, whether or not the function of a liver graft before perfusion is satisfactory can be determined.

(Clause 11) A program for evaluating a function of an organ for transplantation described in Clause 11 evaluates a function of an organ for transplantation harvested from a living body with a computer including a computing unit. The program causes the computing unit to perform preparing data representing change over time in contents of marker substances in accordance with a perfusion, taking a first tissue sample from the organ for transplantation at first timing in a reperfusion of the organ for transplantation, taking a second tissue sample from the organ for transplantation at second timing after the first timing in the reperfusion, measuring contents of the marker substances in the first tissue sample, measuring contents of the marker substances in the second tissue sample, calculating change in content at the second timing as compared with the first timing for each of the marker substances, and calculating an indicator relating to evaluation of the function of the organ for transplantation using the calculated change in content and the data.

According to the program described in Clause 11, by expressing change in content of each of marker substances during reperfusion as an indicator, whether or not an organ for transplantation is transplantable can be determined based on the indicator. Thus, whether or not an organ for transplantation is transplantable can objectively be determined before transplantation. Possibility of use for transplantation also of an organ from a donor after circulatory death the function of which has been recovered by reperfusion is enhanced, which can contribute to solution of lack of donor organs.

(Clause 12) An apparatus that evaluates a function of an organ for transplantation described in Clause 12 includes a computing unit. The apparatus prepares data representing change over time in contents of marker substances in accordance with a perfusion. The computing unit measures contents of the marker substances in a first tissue sample taken from the organ for transplantation at first timing in a reperfusion of the organ of the reperfusion. The computing unit measures contents of the marker substances in a second tissue sample taken from the organ for transplantation at second timing after the first timing in the reperfusion. The computing unit calculates change in content at the second timing as compared with the first timing for each of the marker substances and calculates an indicator relating to evaluation of the function of the organ for transplantation using the calculated change in content and the data.

According to the apparatus that evaluates the function described in Clause 12, by expressing change in content of each of marker substances during reperfusion as an indicator, whether or not an organ for transplantation is transplantable can be determined based on the indicator. Thus, whether or not an organ for transplantation is transplantable can objectively be determined before transplantation. Possibility of use for transplantation also of an organ from a donor after circulatory death the function of which has been recovered by reperfusion is enhanced, which can contribute to solution of lack of donor organs.

It should be understood that the embodiment disclosed herein is illustrative and non-restrictive in every respect. The scope of the present invention is defined by the terms of the claims rather than the description above and is intended to include any modifications within the scope and meaning equivalent to the terms of the claims.

REFERENCE SIGNS LIST

1 liver; 10 storage container; 12 perfusate flow-in cannula; 14 perfusate flow-out cannula; 20 perfusate flow-in pathway; 22 pump; 30 perfusate flow-out pathway; 40 bile flow-out cannula; 50, 60 perfusate reservoir; 70 gas exchange mechanism; 80 container; 100 mass spectrometer; 102 LC/MS unit; 104 data processor; 106 controller; 120 evaluation apparatus; 122 CPU; 124 storage; 126 display; 128 input unit

The invention claimed is:

1. A method of transplanting of a liver for transplantation harvested from a living body for treatment of liver failure, the method comprising:

measuring contents of marker substances in a first tissue sample that is taken from the liver for transplantation at a first timing in a reperfusion of the liver for transplantation;

measuring contents of the marker substances in a second tissue sample that is taken from the liver for transplantation at a second timing after the first timing in the reperfusion;

calculating a change including an increase or a decrease in content at the second timing as compared with the first timing for each of the marker substances;

calculating an indicator relating to evaluation of the function of the liver for transplantation using the calculated change in content and data representing change over time in contents of the marker substances in accordance with a perfusion, wherein the marker substances include at least two of sedoheptulose 7-phosphate, adenosine triphosphate, glucose-6-phosphate, succinyl coenzyme A (CoA), dimethylglycine, choline, 2-aminobutyric acid, uric acid, pyruvic acid, and inosine, wherein the calculating change includes calculating a tendency of change in the content, and the calculating an indicator includes expressing the tendency of change in the content for each marker substance measured as a numerical score, the expressing the tendency as the numerical score includes setting a score at a time when the tendency of change in the content in the liver for transplantation agrees with the tendency of change in the content in a liver having normal function to be larger than a score at a time when the tendency of change in the content in the liver for transplantation does not agree with the tendency of change in the content in the liver having normal function;

expressing the tendency of change for all of the marker substances measured as a total numerical score; and comparing the total numerical score with a numerical threshold score and transplanting the liver for transplantation to a recipient if the total numerical score is larger than the numerical threshold score;

wherein the numerical threshold score is set between the range of total numerical scores of normal livers and mild DCD (Donation after Circulatory Death) livers and the range of total numerical scores of severe DCD livers.

2. The method of evaluating a function of a liver for transplantation according to claim 1, wherein each of the measuring contents of the marker substances in the first tissue sample and the measuring contents of the marker substances in the second tissue sample includes measuring contents of the marker substances by mass spectrometry.

3. The method of evaluating a function of a liver for transplantation according to claim 1, wherein the calculating change further includes making a determination of the increase in the content when a rate of change in the content at the second timing as compared with the content at the first timing is higher than a first threshold value larger than one, and making a determination of the decrease in the content when the rate of change is lower than a second threshold value smaller than one.

4. The method of evaluating a function of a liver for transplantation according to claim 1, wherein after harvesting from a donor, the liver for transplantation is cold-preserved until the reperfusion, and the method further comprises:

measuring a content of a first marker substance by mass spectrometry of a third tissue sample that is taken from the liver for transplantation at third timing before start of cold preservation;

measuring a content of the first marker substance by mass spectrometry of a fourth tissue sample that is taken from the liver for transplantation at fourth timing after end of the cold preservation and before start of the reperfusion; and determining whether the function of the liver for transplantation is normal based on the contents of the first marker substance at the third timing and the fourth timing.

5. The method of evaluating a function of a liver for transplantation according to claim 1, wherein after harvesting from a donor, the liver organ for transplantation is cold-preserved until the reperfusion, and the method further comprises:

measuring a content of a first marker substance by mass spectrometry of the fourth tissue sample that is taken from the liver for transplantation at fourth timing after end of cold preservation and before start of the reperfusion; and determining whether the function of the liver for transplantation is normal based on the content of the first marker substance at the fourth timing.

6. The method of evaluating a function of a liver for transplantation according to claim 1, wherein after harvesting from a donor, the liver for transplantation is cold-preserved until the reperfusion, and the method further comprises:

measuring contents of first and second marker substances by mass spectrometry of the third tissue sample that is taken from the liver for transplantation at third timing before start of cold preservation; and determining whether the function of the liver for transplantation is normal based on the contents of the first and second marker substances at the third timing.

7. The method of evaluating a function of a liver for transplantation according to claim 4, wherein the first marker substance is uridine.

8. The method of evaluating a function of a liver for transplantation according to claim 6, wherein the first marker substance is uridine, and the second marker substance is adenylosuccinic acid.

* * * * *